(12) United States Patent
Kim et al.

(10) Patent No.: US 11,382,940 B2
(45) Date of Patent: Jul. 12, 2022

(54) LACTOBACILLUS SALIVARIUS CJLS1511, ANIMAL FEED ADDITIVE COMPOSITION COMPRISING SAME BACTERIUM OR DEAD CELLS THEREOF, AND METHOD FOR PRODUCING SAME DEAD CELLS

(71) Applicant: CJ CHEILJEDANG CORPORATION, Seoul (KR)

(72) Inventors: Ji Eun Kim, Uiwang-si (KR); Kyeong Su Chae, Bucheon-si (KR); Sung Hun Kim, Siheung-si (KR); Seok Woo Chee, Seoul (KR); Joong Su Lee, Gimpo-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 257 days.

(21) Appl. No.: 16/324,462

(22) PCT Filed: Aug. 7, 2017

(86) PCT No.: PCT/KR2017/008487
§ 371 (c)(1),
(2) Date: Feb. 8, 2019

(87) PCT Pub. No.: WO2018/030730
PCT Pub. Date: Feb. 15, 2018

(65) Prior Publication Data
US 2019/0216867 A1 Jul. 18, 2019

(30) Foreign Application Priority Data
Aug. 9, 2016 (KR) ......................... 10-2016-0101355

(51) Int. Cl.
*A61K 35/747* (2015.01)
*C12N 1/20* (2006.01)
*C12R 1/225* (2006.01)
*A23K 50/75* (2016.01)
*A23K 10/16* (2016.01)

(52) U.S. Cl.
CPC ............ *A61K 35/747* (2013.01); *A23K 10/16* (2016.05); *A23K 50/75* (2016.05); *C12N 1/20* (2013.01); *C12N 1/205* (2021.05); *A23Y 2220/79* (2013.01); *C12R 2001/225* (2021.05)

(58) Field of Classification Search
CPC ...... A61K 35/747; A23K 50/75; C12R 1/225; C12N 1/20
See application file for complete search history.

(56) References Cited

U.S. PATENT DOCUMENTS

| | | |
|---|---|---|
| 8,101,170 B2 | 1/2012 | Plail et al. |
| 2006/0078547 A1 | 4/2006 | Collins et al. |
| 2010/0080783 A1* | 4/2010 | Watson ............... A23K 10/18 424/93.45 |
| 2013/0309357 A1* | 11/2013 | Mercenier ............ A23K 10/18 426/61 |
| 2013/0330308 A1* | 12/2013 | Millan ................ A61K 35/747 424/93.41 |

FOREIGN PATENT DOCUMENTS

| | | |
|---|---|---|
| CN | 1639317 A | 7/2005 |
| CN | 101971921 A | 2/2011 |
| CN | 102373162 A | 3/2012 |
| CN | 102373162 A | 9/2012 |
| CN | 102660478 A | 9/2012 |
| CN | 102725397 A | 10/2012 |
| CN | 105331559 A | 2/2016 |
| CN | 107949633 A | 4/2018 |
| CN | 110878267 A | 3/2020 |
| EP | 1409645 B1 | 8/2009 |
| EP | 2647694 B1 | 12/2017 |
| GB | 2469059 A | 10/2010 |
| JP | 4176715 B2 | 8/2008 |
| KR | 1998078358 A | 11/1998 |
| KR | 1020080011901 A | 2/2008 |
| KR | 1020090057154 A | 6/2009 |
| KR | 1020110009516 A | 1/2011 |
| KR | 1020120047792 A | 5/2012 |
| KR | 1020130059950 A | 6/2013 |
| KR | 1020130088816 A | 8/2013 |
| KR | 1020140049399 A | 4/2014 |
| RU | 2372788 C2 | 11/2009 |
| WO | 2004003235 A2 | 1/2004 |
| WO | 2012037015 A2 | 3/2012 |
| WO | 2012060579 A2 | 5/2012 |

OTHER PUBLICATIONS https://en.wikipedia.org/wiki/Anticaking_agent (Year: 2021).*
Ashraf et al., "Effect of cell-surface components and metabolites of lactic acid bacteria and probiotic organisms on cytokine production and induction of CD25 expression in human peripheral mononuclear cells", J Dairy Science, May 2014;97(5):2542-58. doi: 10.3168/jds. 2013-7459 (Year: 2014).*
Taverniti et al., "The immunomodulatory properties of probiotic microorganisms beyond their viability (ghost probiotics: proposal of paraprobiotic concept)", Genes Nutr. Aug. 2011; 6(3): 261-274 (Year: 2011).*
Zhang et al. "Different combinations of probiotics improve the production performance, egg quality, and immune response of layer hens", Poultry Science Nov. 2012; 91(11): 2755-60, doi: 10.3382/ps.2012-02339 (Year: 2012).*
English translation of Office Action dated Oct. 17, 2019 of Russian Patent Application No. 2019104984, which corresponds to the above-identified application.
Office Action dated Oct. 17, 2019 of Russian Patent Application No. 2019104984, which corresponds to the above-identified application.
Extended European search report dated Dec. 19, 2019 of European patent application No. 17839748.5, which corresponds to the above-identified patent application.

(Continued)

*Primary Examiner* — Ruth A Davis
(74) *Attorney, Agent, or Firm* — Cantor Colburn LLP

(57) ABSTRACT

The present invention relates to *Lactobacillus salivarius* CJLS1511, a composition for animal feed additives comprising the same or its inactivated bacterial cells, and a method for preparing the inactivated bacterial cells.

15 Claims, 2 Drawing Sheets

(56) References Cited

OTHER PUBLICATIONS

Korean Notice of Allowance for KR10-2016-0101355 (priority application), dated Apr. 12, 2018, 3 pp.
Korean Office Action for KR10-2016-0101355 (priority application), dated Sep. 6, 2017, 5 pp.
Scott A. McEwen, et al., "Antimicrobial Use and Resistance in Animals", Clinical Infectious Diseases, 2002, 34 (Suppl 3):S93-S106 (14 pp.).
International Search Report, dated Nov. 17, 2017, for PCT/KR2017/008487 (2 pages) (English).
Chen, Xinliang et al., "Isolation and Identification of Lactobacillus salivarius from Chicken Intestine and Its Biological Characteristics," Food Science, 2016, vol. 37, No. 13, pp. 157-161; English Abstract.
Li Hai-long et al., "Advances in Saliva Lactobacillus (Lactobacillus salivarius," Journal of Microbiology, Oct. 2015, vol. 35, No. 5, pp. 94-97; English Abstract.
M. Garriga et al., "Selection of lactobacilli for chicken probiotic adjuncts," Journal of Applied Microbiology, 1998, vol. 84, pp. 125-132.
Office Action dated Jul. 20, 2021 of CN Patent Application No. 201780049252.5.
Wang Li-hong, "Isolation of lactic acid bacteria and their effects on broiler production performance," Thesis for Master's Degree Northwest A&F University in 2014, pp. 1-45, Postgraduate No. 2011050609; English Abstract.

\* cited by examiner

LACTOBACILLUS SALIVARIUS CJLS1511, ANIMAL FEED ADDITIVE COMPOSITION COMPRISING SAME BACTERIUM OR DEAD CELLS THEREOF, AND METHOD FOR PRODUCING SAME DEAD CELLS

TECHNICAL FIELD

The present invention relates to a novel *Lactobacillus salivarius* CJLS1511, a composition for adding animal feed comprising the same or inactivated bacterial cells thereof, and a method for preparing the inactivated bacterial cells.

BACKGROUND ART

*Lactobacillus* sp. microorganism is a lactic acid *bacillus* that performs homofermentation or heterofermentation, and is commonly found in intestines of animals including human, and a fermentation process of dairy products and vegetables. *Lactobacillus* sp. microorganism is lactic acid producing bacteria commonly found in intestinal tract in animals, and performs homofermentation or hetero-fermentation using dairy products and vegetables as its substrates. *Lactobacillus* sp. microorganism is known to maintain intestinal environment as acidic condition in animals, inhibit overgrowth of harmful bacteria such as *E. coli* and *Clostridium*, improves diarrhea and constipation in animals, and help vitamin synthesis, and decrease serum cholesterol level, and have anti-cancerous activity, etc.

Studies have been conducted on the probiotics as feed additives according to the aforementioned properties of the *Lactobacillus* sp. microorganism. Bacterial diarrhea in livestock results in reduction of a growth rate and survival rate. Therefore, in order to increase livestock productivity, various antibiotics have been added to animal diet at a pharmaceutical dose. In recent years, however, the problem of antibiotic resistance has been discussed in worldwide because of its excessive use. Accordingly, governments in many countries have started to limit the usage of the antibiotics in animal feed. (Korean Patent Laid-Open Publication No. 10-1998-78358) (McEwen and Fedorka-Cray, Antimicrobial use and resistance in animals, Clinical infectious Diseases, Volume 34, June 2002, pages S93-S106).

RELATED ART DOCUMENT (Patent Document 1) Korean Patent Laid-Open Publication No. 10-1998-78358

NON-RELATED ART DOCUMENT (Non-Patent Document 1) Clinical infectious Diseases, Volume 34, June 2002, pages S93-S106

Technical Problem

The present invention provides a novel *Lactobacillus* sp. microorganism-containing feed additives capable of enhancing animal's body weight gain, immune status, anti-disease ability of animals and inhibiting overgrowth of harmful bacteria in intestinal tract of the animals.

Technical Solution

According to an exemplary embodiment of the present invention, there are provided *Lactobacillus salivarius* CJLS1511 (KCCM11829P) or inactivated bacterial cells thereof.

According to another exemplary embodiment of the present invention, there is provided a composition for an animal feed additive comprising *Lactobacillus salivarius* CJLS1511 (KCCM11829P) or inactivated bacterial cells thereof.

According to another exemplary embodiment of the present invention, there is provided in the form of an animal feed additive as described above.

According to another exemplary embodiment of the present invention, there is provided a method for preparing the inactivated *Lactobacillus salivarius* CJLS1511 (KCCM11829P), comprising:

culturing *Lactobacillus salivarius* CJLS1511 (KCCM11829P) to prepare a culture solution, heating the culture solution at a certain temperature ranging from 70 to 160° C., cooling down the heated culture solution to a certain temperature ranging from 10 to 60V, and isolating inactivated *Lactobacillus salivarius* CJLS1511 (KCCM11829P) from the cooled culture solution.

Advantageous Effects

*Lactobacillus salivarius* CJLS1511 according to an exemplary embodiment of the present invention or inactivated bacterial cells thereof may be excellent in abilities of degradation of neutral lipid, adsorption of endotoxin, inhibition of pathogenic bacterial growth, and enhancing digestive enzyme activity.

Compositions for the animal feed additives or its mixed feed, comprising *Lactobacillus salivarius* CJLS1511 according to an exemplary embodiment of the present invention or inactivated bacterial cells thereof, may enhance animal growth performance and improve immune status thereby help the animal fight against pathogen-derived disease.

DETAILED DESCRIPTION OF EMBODIMENTS

Hereinafter, the present invention will be described in detail. Descriptions not described in the specification can be sufficiently recognized and deduced by a person skilled in the technical field or fields similar to this, and thus, details thereof will be omitted.

According to an exemplary embodiment of the present invention, there is provided *Lactobacillus salivarius* CJLS1511 (KCCM11829P) or its inactivated bacterial cells.

The "inactivated bacterial cells of the *Lactobacillus salivarius* CJLS1511 (KCCM11829P)" may be for examples, dead *Lactobacillus salivarius* CJLS1511 (KCCM11829P), more specifically, heat-inactivated *Lactobacillus salivarius* CJLS1511.

The present inventors collected the end of small intestine from broiler, washed with sterile distilled water streaked on MRS medium supplemented with 0.001% bromphenicol purple (BCP), and anaerobically cultured at 37° C. Here, about 50 lactic acid-producing strains were selected and subcultured. These strains were subjected to secondary isolation by morphological separation method, thereby obtaining 24 kinds of bacilli. 24 kinds of the bacilli were subjected to tertiary isolation by comparison in view of antibacterial activity and digestive enzyme activity ability, thereby obtaining 10 strains. Bile resistance, acid resistance, and animal intestinal cell wall adhesion ability of the lactic acid-producing strains were measured, and among them, one strain in which sugar fermentation, inhibition of pathogenic bacterial growth, digestive enzyme activity, and degradation of a neutral lipid are the most excellent, was isolated.

The isolated lactic acid-producing strain was designated as *Lactobacillus salivarius* CJLS1511 and deposited on Apr. 12, 2016 (Accession No.: KCCM11829P) in the Korean Culture Center of Microorganisms (KCCM).

The morphological and physiological characteristics of *Lactobacillus salivarius* CJLS1511 are shown in Table 1 below.

TABLE 1

| 1. Morphological characteristics (morphology when grown in MRS solid medium) | |
| --- | --- |
| Cell shape | *Bacillus* |
| Polymorphism of cells | No |
| Mobility | No |
| Apo formation | No |
| 2. Physiological characteristics | |
| Gram staining | Gram positive |
| Catalase | Negative |
| Oxidase | Negative |
| Growth temperature and time | 37° C., 18 to 48 hr |
| Oxygen requirement | Facultative anaerobic |

Figure 1:
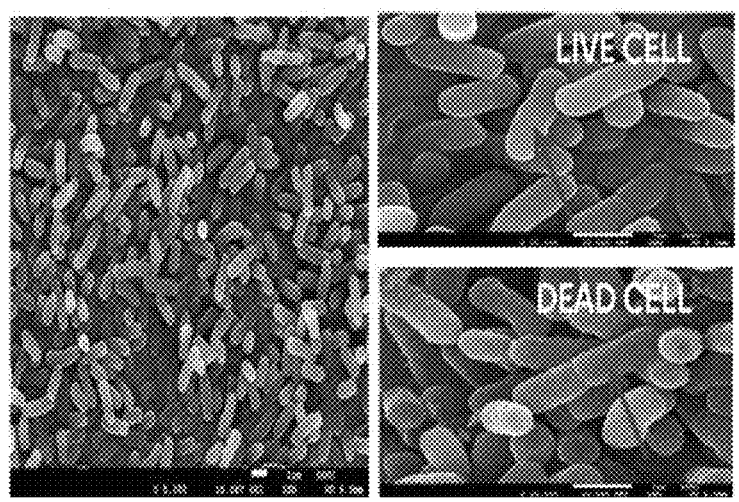
FIG. 1 shows an electron microscopic image of *Lactobacillus salivarius* CJLS1511 strain or its inactivated bacterial cells.

In addition, *Lactobacillus salivarius* CJLS1511 has a rod shape as shown in FIG. 1, and does not form spores. When the strain is killed, difference between live cells and dead cells is confirmed by glycoprotein activity on a cell wall surface.

Figure 2:
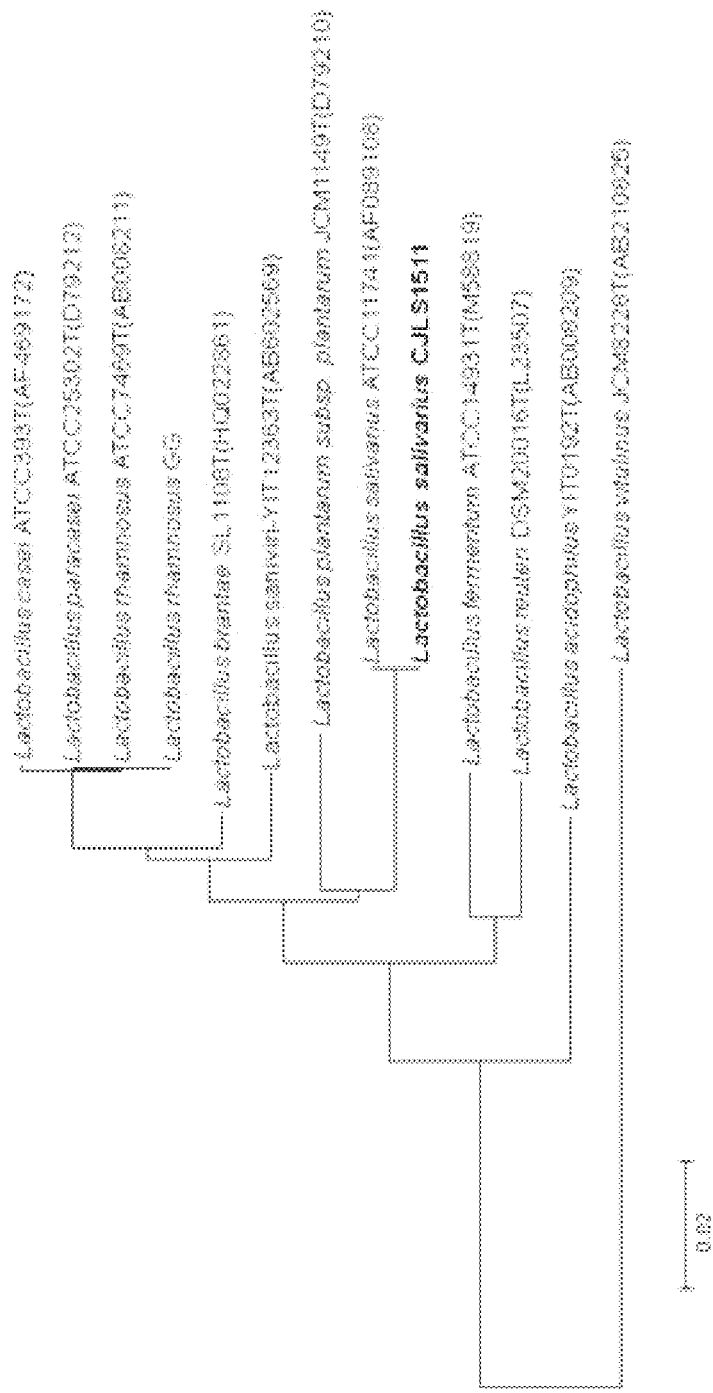
FIG. 2 shows phylogenetic tree of *Lactobacillus salivarius* CJLS1511.

Biochemical analysis of *Lactobacillus salivarius* CJLS1511 was conducted by using an API kit. As a result, it was identified as carbohydrates fermentability similar to that of *Lactobacillus salivarius* ATCC11741 or KCCM 40210 standard strain, as shown in Table 2 below. According to 16s rRNA analysis which was performed by Macrogen, Inc., it was identified as having molecular biological properties 99% similar to that of *Lactobacillus salivarius* ATCC11741 or KCCM 40210 standard strain, as shown in FIG. 2.

TABLE 2

Analysis of sugar utilization of *Lactobacillus salivarius* CJLS1511

| No. | carbohydrates type | *Lactobacillus salivarius* CJLS1511 |
| --- | --- | --- |
| 0 | Temoin | − |
| 1 | Glycerol | − |
| 2 | Erythritol | − |
| 3 | D-arabinose | − |
| 4 | L-arabinose | − |
| 5 | D-ribose | − |
| 6 | D-xylose | − |
| 7 | L-xylose | − |
| 8 | D-adonito | − |
| 9 | Methyl-αD-xylopyranozide | + |
| 10 | D-galactose | + |
| 11 | D-glucose | + |
| 12 | D-fructose | + |
| 13 | D-mannose | − |
| 14 | L-sorbose | − |
| 15 | L-ramnose | − |
| 16 | D-ulcitol | − |
| 17 | Inositol | + |
| 18 | D-mannitol | + |
| 19 | D-sorbitol | + |
| 20 | Methyl-αD-manopyranozide | − |
| 21 | Methyl-αD-glucopyranozide | − |
| 22 | N-acetylglucosamine | + |
| 23 | Amygdalin | − |
| 24 | Arbutin | + |
| 25 | Asculin | − |
| 26 | Salicin | + |
| 27 | D-celobiose | − |
| 28 | D-maltose | + |
| 29 | D-lactose | + |
| 30 | D-mellibiose | + |
| 31 | D-saccharose | + |
| 32 | D-trehalose | + |
| 33 | Inulin | − |
| 34 | D-melesitose | − |
| 35 | D-rafinose | + |
| 36 | Amidon | − |
| 37 | Glycogen | − |
| 38 | Xylitol | − |
| 39 | Genthiobiose | − |
| 40 | D-turanose | − |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | Gluconate | − |
| 48 | 2-ketogluconate | − |
| 49 | 5-ketogluconate | − |

The *Lactobacillus salivarius* CJLS1511 (KCCM11829P) may be excellent in acid resistance, bile resistance, antimicrobial activity, of digestive enzyme activity, and degradation of neutral lipid, and may effectively improve feed efficiency and animal's body weight gain when used as animal feed additives or its mixed feed.

The inactivated *Lactobacillus salivarius* CJLS1511 (KCCM11829P) exhibits competitive adhesion inhibition with intestinal harmful bacteria, thereby contributing to formation of intestinal flora, and a lipoteichoic acid, which is a cell wall component that is eluted while cellular membrane of the inactivated bacterial cells are destroyed in a small intestine, may interfere with colonization of intestinal noxious bacteria in the intestinal mucosa. In addition, the inactivated *Lactobacillus salivarius* CJLS1511 (KCCM11829P) have higher hydrophobicity and flocculability than those of live cells, and thus, may attach to pathogenic microorganisms and endotoxins better than live cells do, thereby improving the anti-disease ability. Further, when animals are fed with the inactivated microbes of *Lactobacillus salivarius* CJLS1511 (KCCM11829P), both of the animal's body weight and a feed conversion ratio may be improved.

*Lactobacillus salivarius* CJLS1511 (KCCM11829P) or its inactivated bacterial cells may further include a protective agent. Examples of the protective agent include at least one among yeast, yeast extract, monosaccharides, polysaccharides, starches, and sugars such as raw sugar and refined sugar. Specifically, the protective agent may include at least one selected from the group consisting of yeast extract, dextrose and raw sugar. When the protective agent is used, it is possible to prevent *Lactobacillus salivarius* CJLS1511

(KCCM11829P) or its inactivated bacterial cells from external environment to prevent contamination, and to prolong its shelf life.

According to another exemplary embodiment of the present invention, there is provided a composition for an animal feed additive comprising *Lactobacillus salivarius* CJLS1511 (KCCM11829P) or its inactivated bacterial cells. Specifically, the composition for an animal feed additive may include inactivated bacterial cells of *Lactobacillus salivarius* CJLS1511 (KCCM11829P).

The composition for the animal feed additives may further include an excipient. The excipient is not particularly limited, and may be any excipient that is conventionally used in the art. Examples of excipient may include saccharides such as lactose, D-mannitol, D-sorbitol, sucrose, etc., gums such as xanthan gum, guar gum, arabic gum, etc., starches such as corn starch, potato starch, etc., inorganic salts such as calcium phosphate, calcium sulfate, precipitated calcium carbonate, etc.

The composition for the animal feed additives may include the above-described *Lactobacillus salivarius* CJLS1511 (KCCM11829P) or its inactivated bacterial cells in an amount of $1.0 \times 10^8$ cfu to $1.0 \times 10^{10}$ cfu per 1 g of the composition. Specifically, the amount may be $1.0 \times 10^8$ cfu to $3.0 \times 10^9$ cfu, and may be $5 \times 10^8$ cfu per 1 g of the composition as an example.

The composition for animal feed additives may have a form of powders, pellets, granules, and the like. The amount of *Lactobacillus salivarius* CJLS1511 (KCCM11829P) or its inactivated bacterial cells in the composition for animal feed additives may have a range of 0.1 wt % to 10 wt %, specifically 0.1 wt % to 7 wt %. When the composition includes the strain or its inactivated bacterial cells in the above-described range, it is possible to maximize degradation of neutral lipid, adsorption of endotoxin, inhibition of pathogenic bacterial growth, and increase of digestive enzyme activity of the composition for adding to animal diet.

According to another exemplary embodiment of the present invention, there is provided animal feed prepared by using the composition for animal feed additives as described above. The animal feed may be prepared by mixing the composition for animal feed additives according to exemplary embodiments of the present invention with a conventional animal feed. An amount of the composition for animal feed additives of the present invention in the animal feed may be from 0.1 wt % to 1 wt % of the total weight of the animal feed.

The animal feed is not particularly limited, and may be feed for domestic animals. The term "domestic animal" refers to animals and pets for producing livestock products and aquatic products that are useful for human beings, such as milk, meat, eggs, hair, leather, feathers, etc. Specifically, the animal feed is provided to domestic animals such as dogs, cows, chickens, pigs, horses, etc. More specifically, it may be provided to poultry, more specifically, a broiler.

The animal feed may include components such as carbohydrates, proteins, lipids, vitamins, minerals, etc., those are essential nutrients for the animal growth. The 'protein' may be an animal protein or a vegetable protein, for example, meat, poultry, fish meal, soy protein, milk protein, gluten, or the like. Examples of the 'carbohydrate' may include cereals or beans such as corn, rice, wheat, barley, oats, soybeans or mixtures thereof. The 'lipid' may be an animal fat, a vegetable fat, and meat-derived fats, or the like. Otherwise, it is possible to further include other components which add functionality to the animal feed in addition to the above-described component. Alternatively, sugars, salts, spices, seasoning, flavoring enhancer, and the like may be incorporated.

According to another exemplary embodiment of the present invention, there is provided a method for preparing inactivated bacterial cells of *Lactobacillus salivarius* CJLS1511 (KCCM11829P), comprising:

culturing *Lactobacillus salivarius* CJLS1511 (KCCM11829P) to prepare a culture solution, heating the culture solution at a temperature of 70 to 160° C., cooling the heated culture solution to a temperature ranging from 10 to 60° C., and isolating inactivated bacterial cells of *Lactobacillus salivarius* CJLS1511 (KCCM11829P) from the cooled culture solution.

Specifically, in step of culturing the *Lactobacillus salivarius* CJLS1511 (KCCM11829P) to prepare a culture solution, agar medium, specifically, an MRS medium may be used. The culturing may be performed at 25° C. to 40° C. for 5 to 48 hours, more specifically at 30 to 40° C. for 12 to 36 hours, more specifically at 35 to 40° C. for 20 to 30 hours, thereby preparing the culture solution.

Then, the culture solution is heated at a temperature of 70° C. to 160° C. The heating may be performed by direct heating means or indirect heating means, but may be performed by indirect heating means such as a heat exchanger. The heating may be performed at a temperature range of 80° C. to 150° C., more specifically, 90° C. to 120° C. The *Lactobacillus salivarius* CJLS1511 may be inactivated or killed by the heating.

The heated culture solution may be rapidly cooled to a temperature of 10° C. to 60° C., specifically 20° C. to 50° C., or in an example, may be rapidly cooled up to 4° C. The cooling may be performed at a rate of 10° C./min to 60° C./min, specifically 20° C./min to 50° C./min, more specifically, 30° C./min to 40° C./min. Then, the inactivated bacterial cells may be separated from the cooled culture solution to obtain inactivated bacterial cells of *Lactobacillus salivarius* CJLS1511 (KCCM11829P).

The method for preparing inactivated bacterial cells of *Lactobacillus salivarius* CJLS1511 (KCCM11829P) may further comprise mixing the separated inactivated bacterial cells with a protective agent. Further, after that, the method may further comprise pulverizing the obtained mixture of the inactivated bacterial cells and the protective agent. By mixing the protective agent as described above and pulverizing the mixture, it is possible to prevent the inactivated bacterial cells from being contaminated from the external environment and to facilitate distribution of the inactivated bacterial cells.

The protective agent is not particularly limited, but for example, may be at least one among yeast, yeast extract, monosaccharides, polysaccharides, starches, and sugars such as raw sugar and refined sugar. Specifically, the protective agent may include at least one selected from the group consisting of yeast extract, dextrose and raw sugar.

The pulverization may be performed by lyophilization, spray drying, or spray flocculation. More specifically, spray drying may be used. The spray drying is also referred to as atomizer drying, and is a method in which a liquid is sprayed at one time in a hot stream to instantaneously obtain a dried product in a liquid phase. As a method for spraying liquid, there are a centrifugal spray method using a rotary disk and a pressurized spray method using a pressure nozzle. In order to perform the spray drying on skim milk, etc., a known spray drying apparatus employing these spray methods may be used.

In consideration of simplicity of operation, it is preferable that the inactivated bacterial cells and the protective agent is mixed to prepare a mixture, then the mixture is suspended in water, the obtained suspension is subjected to spray drying, wherein specifically, a temperature of an inlet of hot air is 120 to 200° C., preferably 130 to 170° C., and a temperature of an outlet is 30 to 150° C., preferably, 50 to 100° C. An amount of the protective agent to be added may be 0.1 to 300 parts by weight, specifically 0.1 to 200 parts by weight, based on 100 parts by weight of the inactivated bacterial cells.

As an example, an amount of the yeast or yeast extract to be added is 0.04 to 50 parts by weight, preferably 0.1 to 10 parts by weight, an amount of the monosaccharides to be added is 1 to 100 parts by weight, preferably 10 to 50 parts by weight, and an amount of the sugars to be added is 0.2 to 50 parts by weight, preferably 0.4 to 10 parts by weight.

It was confirmed that when a physiologically acceptable inorganic substances such as calcium carbonate, etc., which are hardly soluble in water, as an additive in the pulverization operation, particularly in the spray drying operation, the operation was easily performed. Here, an amount of the inorganic substance in the composition for adding animal feed is 1 to 99 wt %, specifically 1 to 90 wt %, and more specifically 1 to 10 wt %. As an example, the composition for animal feed additives contains 0.05 to 50 wt %, preferably 0.5 to 20 wt %, more preferably 0.5 to 15 wt % of the inactivated bacterial cells powder, and 5 to 80 wt %, preferably 5 to 50%, and more preferably 5 to 20 wt % of the inorganic substance.

The composition for animal feed additives may include the above-described *Lactobacillus salivarius* CJLS1511 (KCCM11829P) or its inactivated bacterial cells in an amount of $1.0 \times 10^8$ cfu to $1.0 \times 10^{10}$ cfu per 1 g of the composition. Specifically, the amount may be $1.0 \times 10^8$ cfu to $3.0 \times 10^9$ cfu, and may be $5 \times 10^8$ cfu in one example.

Hereinafter, constitution and function of the present invention will be described in more detail through preferably exemplary embodiments of the present invention. It is to be noted that Examples to be described below are provided merely for specifically exemplifying the present invention, and accordingly, the present invention is not limited to the following Examples.

Descriptions which are not described in the specification can be sufficiently and technically deduced by a person skilled in the technical field, and accordingly, details thereof will be omitted.

EXAMPLE

Examples 1 to 6

Safety, acid resistance, bile resistance, anti-microbial activity, digestive enzyme activity and triglyceride degradation activity of *Lactobacillus salivarius* CJLS1511 (KCCM11829P) strain of the present invention were evaluated as follows, using *Lactobacillus salivarius* KCCM 40210 known in the art as a reference strain.

Experimental Example 1: Evaluation of Safety of *Lactobacillus salivarius* CJLS1511 (KCCM11829P)

In order to evaluate safety of *Lactobacillus salivarius* CJLS1511 (KCCM11829P) strain, a hemolysis test, a gelatin liquefaction test, confirmation of harmful metabolites (ammonia) occurrence, and a phenylalanine deamination test, were conducted according to a safety evaluation test method presented by Korea Biotechnology Industry Organization standard. Results thereof were shown in Table 3 below.

TABLE 3

| | Item | | | |
|---|---|---|---|---|
| Strain | Gelatin liquefaction test | Phenylalanine deamination test | Hemolysis test | Ammonia test |
| *Lactobacillus salivarius* CJLS1511 | Negative | Negative | α-hemolysis, safe | Negative |

As confirmed in Table 3, it was found that *Lactobacillus salivarius* CJLS1511 (KCCM11829P) was negative in all of the gelatin liquefaction test, the phenylalanine deamination test, and the confirmation of ammonia test, and was safe in the hemolysis test.

Experimental Example 2: Evaluation of Acid Resistance of *Lactobacillus salivarius* CJLS1511 (KCCM11829P)

*Lactobacillus salivarius* CJLS1511 strain that was previously cultured in MRS medium and *Lactobacillus salivarius* KCCM 40210 standard strain which was a comparative strain, were diluted $10^{-6}$ times with MRS solution adjusted to pH 2, 3 and 7, respectively. Each diluted strain solution was cultured at 37° C., streaked on MRS agar medium by a predetermined period of time, and anaerobically cultured for 48 hours. Then, the number of colonies was measured. Results of the acid resistance test were shown in Table 4 below.

TABLE 4

| | MRS broth (pH7) | | | MRS broth (pH2) | | | MRS broth (pH3) | | |
|---|---|---|---|---|---|---|---|---|---|
| | Viable cell count (CFU/mL) | | | Viable cell count (CFU/mL) | | | Viable cell count (CFU/mL) | | |
| Strains | 0 h | 1 h | 3 h | 0 h | 1 h | 3 h | 0 h | 1 h | 3 h |
| *Lactobacillus salivarius* CJLS1511 | $5.8 \times 10^8$ | $6.0 \times 10^8$ | $6.2 \times 10^8$ | $5.8 \times 10^8$ | $2.3 \times 10^5$ | $2.0 \times 10^5$ | $5.8 \times 10^8$ | $3.5 \times 10^8$ | $2.0 \times 10^8$ |
| *Lactobacillus salivarius* KCCM 40210 | $6.4 \times 10^8$ | $6.8 \times 10^8$ | $8.6 \times 10^8$ | $6.4 \times 10^8$ | $2.0 \times 10^2$ | $2.0 \times 10^2$ | $6.4 \times 10^8$ | $1.0 \times 10^8$ | $5.0 \times 10^6$ |

As confirmed from Table 4, *Lactobacillus salivarius* CJLS1511 showed less reduction in viable cell counts than that of *Lactobacillus salivarius* KCCM 40210 standard strain which was a comparative strain, at pH 2 to 4, thereby having excellent acid resistance.

Experimental Example 3: Evaluation of Bile Resistance of *Lactobacillus salivarius* CJLS1511 (KCCM11829P)

*Lactobacillus salivarius* CJLS1511 strain that was previously cultured in MRS medium and *Lactobacillus salivarius* KCCM 40210 standard strain which was a comparative strain, were adjusted to pH 4, respectively, and a concentration of a bile acid solution (Oxgall) was adjusted to 0%, 0.3%, and 1%, respectively, and diluted $10^{-6}$ times with MRS solution. Each diluted strain solution was cultured at 37° C., streaked on MRS agar medium by a predetermined period of time, and anaerobically cultured for 48 hours. Then, the number of colonies was measured. Results of measurement of the viable cell count are summarized in Table 5 below:

TABLE 5

| Strains | MRS broth (pH4) Viable cell count (CFU/mL) | | | MRS broth (pH4) and Oxgall 0.3% Viable cell count (CFU/mL) | | | MRS broth (pH4) and Oxgall 1% Viable cell count (CFU/mL) | | |
|---|---|---|---|---|---|---|---|---|---|
| | 0 h | 1 h | 3 h | 0 h | 1 h | 3 h | 0 h | 1 h | 3 h |
| *Lactobacillus salivarius* CJLS1511 | $2.4 \times 10^8$ | $4 \times 10^8$ | $5.6 \times 10^8$ | $2.4 \times 10^8$ | $4.0 \times 10^6$ | $2.0 \times 10^4$ | $2.4 \times 10^8$ | $5.6 \times 10^5$ | $5.2 \times 10^3$ |
| *Lactobacillus salivarius* KCCM 40210 | $2.0 \times 10^8$ | $2.0 \times 10^8$ | $2.2 \times 10^8$ | $2.0 \times 10^8$ | $2.6 \times 10^5$ | $2.0 \times 10^2$ | $2.0 \times 10^8$ | $2.0 \times 10^2$ | $2.0 \times 10^2$ |

As appreciated from Table 5, the viable cell count of *Lactobacillus salivarius* CJLS1511 was decreased in both of 0.3% and 1% solutions of bile acids (Oxgall) at pH 4. However, the reduction of the viable cell count was much lower than that of *Lactobacillus salivarius* KCCM 40210 standard strain, and thus, it was found that the administered strain could be grown even if the bile acid was endogenously present in the animal body.

Experimental Example 4: Evaluation of Anti-Microbial Activity of *Lactobacillus salivarius* CJLS1511 (KCCM11829P)

Three pathogens (*E. coli* K88, *E. coli* ATCC 25922, *Salmonella typhimurium* KCCM 25922, *Salmonella cholerasuis* KCCM 10709) that were liquid-cultured in a TSB (Tryptic soy broth) medium (BD, USA) for 24 hours were uniformly streaked at $10^{5\sim6}$ cfu/ml using a sterile cotton swab.

After streaking, *Lactobacillus salivarius* CJLS1511 and *Lactobacillus salivarius* KCCM 40210 standard strains were diluted in PBS buffer to $10^9$ cfu/mL, respectively, in a paper disc with a diameter of 4 mm, and then dispensed in 50 μl. The diluted solution was allowed to stand at room temperature until it was sufficiently penetrated into the paper disc, and then aerobically cultured at 37° C. for 18 hours. Here, the diluted solution only included strains that were centrifuged (3,000×g, 10 minutes) for the supernatant after culturing and washed with PBS buffer 3 times. A size of the inhibition ring was measured by a difference between a diameter of the whole transparent ring and a diameter of the agar groove. Results thereof were shown in Table 6 below.

TABLE 6

| Strains | *E. coli* K88 | *E. coli* ATCC 25922 | *Salmonella typhimurium* KCCM 25922 | *Salmonella cholerasuis* KCCM 10709 |
|---|---|---|---|---|
| *Lactobacillus salivarius* CJLS1511 | ++ | ++ | ++ | +++ |
| *Lactobacillus salivarius* KCCM 40210 | + | ++ | + | ++ |

10 to 15 mm: +,
15 to 20 mm: ++,
21 to 25 mm: +++

As confirmed in Table 6, both of *Lactobacillus salivarius* CJLS1511 and the *Lactobacillus salivarius* KCCM 40210 standard strain showed proliferation inhibitory action against pathogenic microorganisms. However, it was confirmed that the *Lactobacillus salivarius* CJLS1511 strain had higher anti-microbial activity than that of the *Lactobacillus salivarius* KCCM 40210 standard strain.

These results were obtained due to the strain itself rather than an effect by the metabolites produced by *Lactobacillus salivarius* CJLS1511, which demonstrated that the growth of harmful microorganisms could be inhibited when applied to livestock.

Experimental Example 5: Evaluation of Digestive Enzyme Activities of *Lactobacillus salivarius* CJLS1511 (KCCM11829P)

An experiment for evaluating degradation activity of digestive enzyme was performed to determine whether the strain was a lactic acid *bacillus* having an enzyme capable of degrading carbohydrate, protein and phosphorus.

To determine whether protease activity was present, skim milk 0.5 (w/v) % was added to an MRS agar medium. To determine whether cellulase activity was present, the MRS agar medium was supplemented with methylcellulose 0.2 (w/v) %. To determine whether α-amylase activity was present, corn starch 0.2 (w/v) % was added to the MRS agar medium. To determine whether phytase activity was present, phytate calcium salt 0.5 (w/v) % was added to the medium. The strains isolated in each of the above-prepared media were streaked, cultured for 24 hours, and observed.

The presence or absence of α-amylase activity and cellulase activity was determined by washing the 24 hour-culture media were treated with a 2% congo red (Sigma, USA) reagent, followed by washing with 1M sodium chloride (NaCl), and confirming the presence or absence of color. Further, the determination of the presence or absence of the protease activity and the phytase activity was confirmed by the presence of the transparent ring, and results thereof were shown in Table 7 below.

TABLE 7

| Strains | Protease activity | Phytase activity | Lipase activity | Cellulose activity | Amylase activity |
|---|---|---|---|---|---|
| Lactobacillus salivarius CJLS1511 | +++ | ++ | + | +++ | +++ |
| Lactobacillus salivarius KCCM 40210 | + | + | ++ | ++ | ++ |

1 to 10 mm: +,
11 to 20 mm: ++,
21 to 30 mm: +++

As confirmed from Table 7, it was found that *Lactobacillus salivarius* CJLS1511 had higher activity of digestive enzymes such as protease activity, phytase activity, cellulose degradation activity, and amylase activity than those of the *Lactobacillus salivarius* KCCM 40210 standard strain.

These results demonstrated that when *Lactobacillus salivarius* CJLS1511 was applied to livestock, feed efficiency could be improved.

Experimental Example 6: Evaluation of Degradation Activity of Neutral Lipid of *Lactobacillus salivarius* CJLS1511 (KCCM11829P)

As a result of searching a bile salt hydrolase (BSH) activity of *Lactobacillus salivarius* CJLS1511, it was confirmed that white precipitate was formed in MRS solid medium supplemented with 2 mM taurodeoxycholate hydrate (TDCA, Sigma, USA), and thus, the enzyme activity was present. Further, sedimentation pattern thereof was similar to that of the *Lactobacillus salivarius* KCCM 40210 standard strain, which was a TDCA positive control strain. However, in the medium supplemented with 2 mM sodium glycodeoxycholate (GDCA, Sigma, USA), the *Lactobacillus salivarius* CJLS1511 strain grew well, but the *Lactobacillus salivarius* KCCM 40210 standard strain showed no precipitation, and did not grow well. Results thereof were shown in Table 8 below.

TABLE 8

| Complex bile acid/strain name | Lactobacillus salivarius CJLS1511 | Lactobacillus salivarius KCCM 40210 |
|---|---|---|
| TDCA | ○ | ○ |
| GDCA | + | − |

○: Precipitation was formed,
X: Precipitation was not formed,
+: Grown,
−: Not grown As appreciated from Table 8, *Lactobacillus salivarius* CJLS1511 had high bile resistance and was converted into a form capable of degrading neutral lipid by the production of BSH, which was found that *Lactobacillus salivarius* CJLS1511 was a functional strain that could affect the body weight when applied to animals.

Preparation Example 1

*Lactobacillus salivarius* CJLS1511 and *Lactobacillus salivarius* KCCM 40210 standard strains were streaked on MRS agar media with a loop, respectively, and cultured at 37° C. for 48 hours to prepare culture solutions.

Then, each culture solution was indirectly heated at a temperature of 100° C. using a heat exchanger, and rapidly cooled up to 10° C. at a rate of 30 to 100 L/min. The inactivated bacterial cells were separated from the rapidly cooled culture solution through a centrifuge (3,000×g, 10 minutes) to prepare inactivated bacterial cells of *Lactobacillus salivarius* CJLS1511 and *Lactobacillus salivarius* KCCM 40210, respectively.

Preparation Example 2

*Lactobacillus salivarius* CJLS1511 and *Lactobacillus salivarius* KCCM 40210 standard strains were streaked on MRS agar media with a loop, respectively, and cultured at 37° C. for 48 hours to prepare culture solutions.

Then, each culture solution was indirectly heated at a temperature of 100° C. using a heat exchanger, and rapidly cooled up to 10° C. at a rate of 30 to 100 L/min. The inactivated bacterial cells were separated from the rapidly cooled culture solution through a centrifuge (3,000×g, 10 minutes) to prepare the inactivated *Lactobacillus salivarius* CJLS1511 and *Lactobacillus salivarius* KCCM 40210, respectively. Then, yeast extract, dextrose, and raw sugar were mixed therewith, respectively. Each mixture was suspended in water, and the obtained suspension was subjected to spray drying to obtain powder. Here, specifically, the spray drying was performed under conditions in which a temperature of an inlet of hot air was 150° C., and a temperature of an outlet was 100° C. As the protective agent, the yeast extract was added in 20 parts by weight, the dextrose was added in 30 parts by weight, and the raw sugar was added in 5 parts by weight, based on 100 parts by weight of the inactivated bacterial cells.

Hydrophobicity and flocculability of the inactivated bacterial cells prepared in Preparation Example 1 were tested by the method described below. The body weight gain and the feed conversion ratio of a basal diet with supplemented the inactivated *Lactobacillus salivarius* CJLS1511 and a basal diet without including the cells were compared with each other.

Experimental Example 7: Evaluation of Hydrophobicity and Co-Aggregation of Live Cells and Inactivated Cells of *Lactobacillus salivarius* CJLS1511 (KCCM11829P)

To confirm the difference in hydrophobicity and flocculability between live cells and inactivated cells of *Lactobacillus salivarius* CJLS1511, a self-flocculation reaction and a co-Aggregation test were evaluated.

The co-Aggregation test was performed by adding 1 mL of toluene to 3 mL of lactic acid *bacillus* diluted so that $OD_{600}$ was 0.5 against the live cells and the inactivated cells of *Lactobacillus salivarius* CJLS1511, followed by vortexing for 90 seconds. Then, each mixture was allowed to stand in a water bath at 37° C. for 1 hour, toluene was removed, and the $OD_{600}$ of the aqueous solution layer was measured.

The co-Aggregation reaction was performed by mixing the live cells and the inactivated cells of *Lactobacillus salivarius* CJLS1511 with pathogenic microorganisms (*E. coli* K88, *Salmonella typhimurium* KCCM 25922, *Salmo-* nella cholerasuis KCCM 10709) in the same amount (pathogenic microorganisms:live cells or dead cells=1:1 (each 1.5 mL)) to prepare a mixture, and adding 1 mL of toluene to 3 mL of the mixture, respectively, followed by vortexing for 90 seconds. Then, each mixture was allowed to stand in a water bath at 37° C. for 1 hour, toluene was removed, and the $OD_{600}$ of the aqueous solution layer was measured.

The hydrophobicity (%) was calculated by 100×(initial $OD_{600}$–$OD_{600}$ after 1 hour)/initial $OD_{600}$.

Results of the self-Aggregation reaction and the co-Aggregation reaction between live cells and inactivated cells were shown in Table 9 below.

TABLE 9

| | | Lactobacillus salivarius CJLS1511 | |
|---|---|---|---|
| Item/pathogenic strain | | Live cells | Inactivated bacterial cell |
| Auto-Aggregarion- | | 11% | 23% |
| Co-Aggregation | E. coli K88 | 54% | 64% |
| | Salmonella typhimurium KCCM 25922 | 45% | 65% |
| | Salmonella cholerasuis KCCM 10709 | 30% | 45% |

As appreciated from Table 9, both of the self-flocculation reaction and the co-Aggregation reaction of inactivated Lactobacillus salivarius CJLS1511 exhibited 1.5 times higher than those of the live cells. It is thought that extracellular hydrophobicity and Aggregation of the microorganisms are affected by the characteristics and surface structure of the cell surface proteins, and the inactivated Lactobacillus salivarius CJLS1511 have increased hydrophobicity and Aggregation due to a different protein structure on cell surface from that of the live cells as shown in FIG. 1. As a result, it is expected to be used as a functional strain that affects anti-disease ability by adhering to the endotoxin.

Experimental Example 8: Comparison of Feed Comprising the Inactivated Lactobacillus salivarius CJLS1511 (KCCM11829P) with Common Basic Feed Broilers were fed with basal diet with supplemented 0.2% (w/w) of the inactivated Lactobacillus salivarius CJLS1511 and basal diet without including the same (control group) for 29 days as the same as a normal feeding period, and initial average body weight (g), final average body weight (g), average daily gain (g/d), average daily feed intake (g/d), and the feed conversion ratio were measured, respectively. Results thereof were shown in Table 10 below.

TABLE 10

| Classification | Control group | Group treated with Lactobacillus salivarius CJLS1511 Inactivated bacterial cells |
|---|---|---|
| Number of test animals | 150 | 150 |
| Initial average body weight (g) | 38.48 | 38.47 |
| Final average body weight (g) | 1582.00$^a$ | 1690.24$^b$ |
| Average daily gain (g/d) | 53.23$^a$ | 56.96$^b$ |
| Average daily feed intake (g/d) | 78.76 | 79.48 |
| Feed conversion ratio | 1.48$^a$ | 1.40$^b$ |

$^{a,\ b}$Means with different characters significantly differ (P < 0.05).

As shown in Table 10, the group treated with the inactivated Lactobacillus salivarius CJLS1511 of the present invention showed superior effects on both of the body weight gain and the feed conversion ratio as compared to those of the control group that were not treated with the inactivated Lactobacillus salivarius CJLS1511.

Name of depository authority: Korean Culture Center of Microorganisms (KCCM) (overseas)
Accession number: KCCM11829P
Accession date: 20160412

The invention claimed is:

1. A composition comprising a spray-dried mixture of inactivated Lactobacillus salivarius CJLS1511 (KCCM11829P) cells and a first protective agent of the inactivated Lactobacillus salivarius CJLS1511 (KCCM11829P) cells,
wherein the first protective agent is at least one selected from the group consisting of yeast and yeast extract,
wherein Lactobacillus salivarius CJLS1511 (KCCM11829P) is characterized by growth in medium supplemented with 2 mM sodium glycodeoxycholate.

2. The composition of claim 1, wherein the composition is used as an animal feed additive.

3. The composition of claim 2, wherein the animal is broiler.

4. Animal feed comprising the composition of claim 2.

5. The composition of claim 1, wherein the composition is in a pulverized state.

6. The composition of claim 1, wherein the spray-dried mixture further comprises a second protective agent of the inactivated Lactobacillus salivarius CJLS1511 (KCCM11829P) cells,
wherein the second protective agent is at least one selected from the group consisting of monosaccharides, polysaccharides, starches, and sugars.

7. The composition of claim 1, wherein the inactivated Lactobacillus salivarius CJLS1511 (KCCM11829P) cells have an amount of 0.1 wt % to 10 wt % of the composition.

8. The composition of claim 1, wherein an amount of the first protective agent is 0.04 parts by weight to 50 parts by weight based on 100 parts by weight of the inactivated Lactobacillus salivarius CJLS1511 (KCCM11829P) cells.

9. The composition of claim 1, wherein inactivated Lactobacillus salivarius CJLS1511 (KCCM11829P) is prepared by a method comprising:
culturing Lactobacillus salivarius CJLS1511 (KCCM11829P) to prepare a culture solution,
heating the culture solution at a temperature of 70 to 160° C.,
cooling the heated culture solution to a temperature ranging from 10 to 60° C., and
isolating inactivated Lactobacillus salivarius CJLS1511 (KCCM11829P) from the cooled culture solution,
mixing the isolated inactivated Lactobacillus salivarius CJLS1511 (KCCM11829P) bacterial cells with a first protective agent, wherein the first protective agent is at least one selected from the group consisting of yeast and yeast extract yeast, and
spray drying the mixture of the isolated inactivated Lactobacillus salivarius CJLS1511 (KCCM11829P) bacterial cells and the first protective agent.

10. A method for preparing inactivated Lactobacillus salivarius CJLS1511 (KCCM11829P), comprising:
culturing Lactobacillus salivarius CJLS1511 (KCCM11829P) to prepare a culture solution,
heating the culture solution at a temperature of 70 to 160° C.,
cooling the heated culture solution to a temperature ranging from 10 to 60° C., isolating inactivated *Lactobacillus salivarius* CJLS1511 (KCCM11829P) from the cooled culture solution, mixing the isolated inactivated *Lactobacillus salivarius* CJLS1511 (KCCM11829P) bacterial cells with a first protective agent, wherein the first protective agent is at least one selected from the group consisting of yeast and yeast extract yeast, and spray drying the mixture of the isolated inactivated *Lactobacillus salivarius* CJLS1511 (KCCM11829P) bacterial cells and the first protective agent.

11. The method of claim 10, wherein the heating is performed by indirect heating through a heat exchanger.

12. The method of claim 10, wherein the cooling is performed at a rate of 10° C./min to 60° C./min.

13. The method of any one of claims 10 to 12, further comprising mixing the isolated inactivated bacterial cells with a protective agent.

14. The method of claim 13, further comprising pulverization of the mixed inactivated bacterial cells.

15. The method of claim 13, further comprising mixing a second protective agent with the isolated inactivated *Lactobacillus salivarius* CJLS1511 (KCCM11829P) bacterial cells, wherein the second protective agent is at least one selected from the group consisting of monosaccharides, polysaccharides, starches, and sugars.

\* \* \* \* \*